US00PP20378P2

(12) United States Plant Patent
Hanes

(10) Patent No.: US PP20,378 P2
(45) Date of Patent: Oct. 6, 2009

(54) ***PELARGONIUM* PLANT NAMED 'AMRI WITS09'**

(50) Latin Name: *Pelargonium hortorum (L.) L' Herit. ex Ait*
Varietal Denomination: Amri Wits09

(75) Inventor: Mitchell Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 12/221,233

(22) Filed: Jul. 31, 2008

(51) Int. Cl.
*A01H 5/00* (2006.01)

(52) U.S. Cl. ..... Plt./326

(58) Field of Classification Search ..... Plt./326
See application file for complete search history.

*Primary Examiner*—Annette H Para
(74) *Attorney, Agent, or Firm*—S. Matthew Edwards

(57) ABSTRACT

A new *Pelargonium* plant named 'Amri Wits09,' particularly distinguished by the clean white flowers with a bold red-purple blotch, light to medium green foliage, round and semi-compact habit, with good branching and garden performance.

1 Drawing Sheet

Latin name of the genus and species of the plant claimed: *Pelargonium hortorum* (*L.*) *L' Herit. ex Ait.*

Varietal denomination: 'Amri Wits09'.

BACKGROUND OF THE NEW PLANT

The present invention comprises a new *Pelargonium*, botanically known as *Pelargonium hortorum*, and hereinafter referred to by the variety name 'Amri Wits09.'

'Amri Wits09' is a product of a planned breeding program. The new cultivar 'Amri Wits09' has clean white flowers with a bold red-purple blotch, light to medium green foliage, round and semi-compact habit, with good branching and garden performance.

'Amri Wits09' originated from a hybridization in a controlled breeding program in Gilroy, Calif. USA. The female parent was an unpatented hybrid seedling identified as '9109-2' with light pink with a blotch flower color. '9109-2' has a smaller blotch size, more pinkish flower color, and is a less vigorous plant than 'Amri Wits09.'

The male parent of 'Amri Wits09' was an unpatented hybrid seedling identified as '9754-1,' a pink with splash color. '9754-1' has a more pinkish flower color, lighter green foliage, and is later to flower than 'Amri Wits09.'

'Amri Wits09' was selected as one flowering plant within the progeny of the stated cross in 2004 in a controlled environment in Gilroy, Calif. USA.

The first act of asexual reproduction of 'Amri Wits09' was accomplished when vegetative cuttings were taken from the initial selection in the November 2004 in a controlled environment in Gilroy, Calif. USA.

Horticultural examination of plants grown from cuttings of the plant initiated in November, 2004 in Gilroy, Calif. USA, and continuing thereafter, has demonstrated that the combination of characteristics as herein disclosed for 'Amri Wits09' are firmly fixed and are retained through successive generations of asexual reproduction.

'Amri Wits09' has not been observed under all possible environmental conditions. The phenotype may vary significantly with variations in environment such as temperature, light intensity and day length.

Plant Breeder's Rights for this cultivar were applied for in Canada on Dec. 24, 2007 and in Europe on Jun. 20, 2008. 'Amri Wits09' has not been made publicly available more than one year prior to the filing of this application.

BRIEF DESCRIPTION OF THE NEW VARIETY

The accompanying photographic drawing shows typical flower and foliage characteristics of 'Amri Wits09' with colors being as true as possible with an illustration of this type. The photographic drawing shows a container of three flowering potted plants of the new variety and a close-up of the flowers.

DETAILED BOTANICAL DESCRIPTION

The measurements were taken in Salinas, Calif. USA, in July, 2008 on plants that were growing in one gallon pots. Culture of these plants started in a greenhouse in April 2008 and were transferred to the outdoors in mid June 2008 under semi-shade. The plants were approximately 4 months old.

Color Chart used: Royal Horticultural Society Colour Chart (R.H.S.) 2001.

BRIEF SUMMARY OF INVENTION

The following observations, measurements, and comparisons describe plants grown outside in Gilroy, Calif., USA. The following traits have been repeatedly observed and are determined to be basic characteristics of the new variety. The combination of these characteristics distinguishes this *Pelargonium* as a new and distinct variety.

TABLE 1

DIFFERENCES BETWEEN THE NEW VARIETY AND A SIMILAR VARIETY

| | 'Amri Wits09' | 'Clips Whitspla' (U.S. Plant Pat. No. 15,630) |
|---|---|---|
| Foliage color | Lighter green | Darker green |
| Peduncle size | Longer | Shorter |
| Flower color | Darker, larger blotches | Lighter, smaller blotches |

Plant:

*Form, growth and habit.*—Upright and rounded growth habit. Well-branched.

*Plant height.*—23–27 cm.

*Plant height* (*inflorescence included*).—30–32 cm.

*Plant width.*—35–40 cm.

Foliage:

*Arrangement.*—Alternate, simple.

*Immature, leaf color, upper surface.*—Between RHS 146A and B. Lower surface: Closest to RHS 146A.

*Mature, leaf color, upper surface.*—Darker than RHS 146A. Lower surface: Closest to RHS 146A.

*Length.*—10–12 cm.

*Width.*—11–15.5 cm.

*Shape.*—Orbicular.

*Base shape.*—Cordate.

*Apex shape.*—Rounded.

*Margin.*—Slightly lobed; irregularly crenate.

*Texture.*—Hirsute, few glandular hairs.

*Color of zone.*—No zone.

*Color of veins, upper surface.*—Indistinct.

*Color of veins, lower surface.*—Between RHS 146A and B.

*Petioles color.*—Between RHS 146A and B.

*Petioles length.*—9.2–11.4 cm.

*Diameter of petiole.*—0.2–0.3 cm.

*Texture.*—Hirsute; glandular hairs.

Stem:

*Color of stem.*—RHS 146B.

*Length of stem.*—15–21 cm.

*Diameter.*—0.6–0.8 cm.

*Length of internodes.*—0.7–1.8 cm.

*Texture.*—Hirsute; glandular hairs.

Inflorescence:

*Type.*—An umbel composed of 15–20 flowers and buds.

*Umbel diameter.*—10–13 cm.

*Umbel depth.*—6–7 cm.

*Color of peduncle.*—RHS 146A.

*Length of peduncle.*—13–19 cm.

*Peduncle diameter.*—0.3–0.4 cm.

*Texture.*—Hirsute; villous; glandular hairs.

*Pedicel color.*—RHS 146B, some have anthocyanin of RHS 176A.

*Length of pedicel.*—3.0–3.5 cm.

*Diameter of pedical.*—0.2 cm.

*Texture.*—Hirsute; glandular hairs.

Corolla:

*Form.*—Polypetalous, overlapping.

*Number of petals.*—5.

*Width of flower.*—4.5–5.2 cm.

*Color upper petals, upper surface.*—Closest to RHS N155B ground color; RHS N57A large blotches, but more red at the center of the blotch with the outer edge of the blotch fading to RHS N57C; RHS 61B veins.

*Color upper petals, lower surface.*—Closest to RHS N155B.

*Length of upper petals.*—3.0–3.1 cm.

*Width of upper petals.*—2.4–2.6 cm.

*Color lower petals, upper surface.*—Closest to RHS N155B ground color; RHS N57A large blotches, but more red at the center of the blotch with the outer edge of the blotch fading to RHS N57C.

*Color lower petals, lower surface.*—Closest to RHS N 155B.

*Petal shape.*—Spathulate.

*Apex shape.*—Rounded.

*Margin.*—Entire.

*Petal texture.*—Papillose, both sides.

*Number of petaloids.*—None.

*Duration of flowering.*—Continuous flowering throughout the Summer.

Bud (when sepals first divide):

*Color.*—RHS 65D (sometimes a few spots of RHS N66A are showing).

*Length.*—0.6–0.8 cm.

*Width.*—1.8–2.3 cm.

*Shape.*—Oblong to elliptic.

*Number of sepals.*—5, fused at the base.

*Color of sepals.*—RHS 146A but lighter.

*Length of sepals.*—1.6–1.7 cm.

*Width of sepals.*—0.3–0.5 cm.

*Sepal shape.*—Lanceolate.

*Apex shape.*—Acute.

*Margins.*—Entire.

*Texture.*—Hirsute; glandular hairs.

Reproductive organs:

*Pistil.*—1.

*Length.*—0.9–1.0.

*Style color.*—RHS 58D.

*Style length.*—0.2 cm.

*Stigma color.*—RHS 58D.

*Number of anthers.*—About 6–7.

*Length filaments.*—0.5–0.7 cm.

*Color of filaments.*—RHS 58A with RHS N155B but whiter basally.

*Pollen amount.*—Moderate.

*Color of pollen.*—RHS N25A.

*Fertility/seed set.*—Not observed on this hybrid.

Disease/pest resistance: Disease resistance and/or susceptibility has not been observed on this hybrid.

What is claimed is:

1. A new and distinct variety of *Pelargonium* plant named 'Amri Wits09,' substantially as illustrated and described herein.

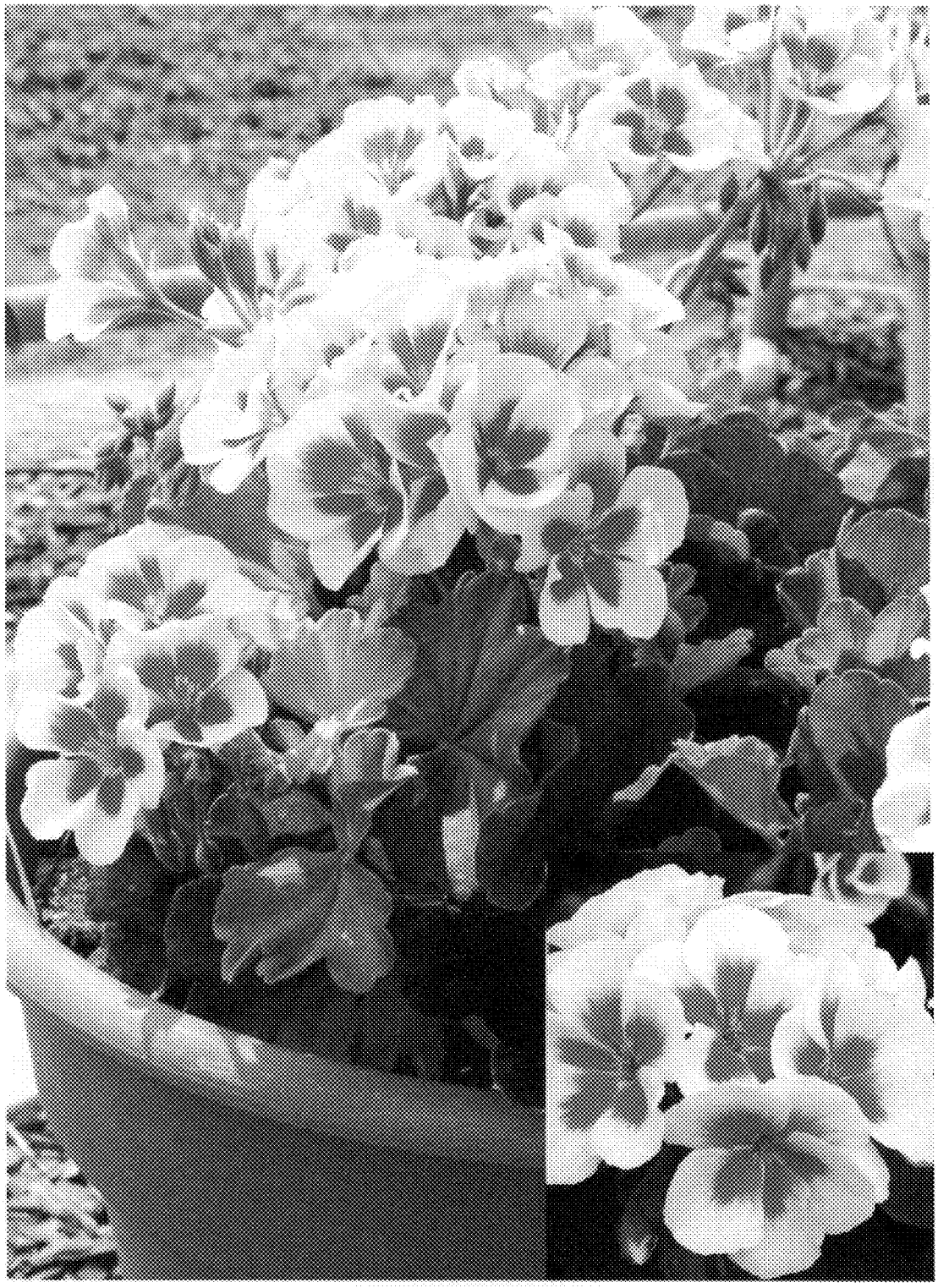

* * * * *